United States Patent
Sibley et al.

(10) Patent No.: US 12,414,935 B2
(45) Date of Patent: Sep. 16, 2025

(54) COMPOUNDS AND METHODS FOR THE TREATMENT OF PARASITIC DISEASES

(71) Applicants: WASHINGTON UNIVERSITY, St. Louis, MO (US); THE BROAD INSTITUTE, INC., Cambridge, MA (US); PRESIDENT AND FELLOWS OF HARVARD COLLEGE, Cambridge, MA (US)

(72) Inventors: Laurence David Sibley, St. Louis, MO (US); Bruno Melillo, Cambridge, MA (US); Eamon Comer, Cambridge, MA (US)

(73) Assignees: Washington University, St. Louis, MO (US); The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 835 days.

(21) Appl. No.: 17/604,732

(22) PCT Filed: Apr. 22, 2020

(86) PCT No.: PCT/US2020/029407
§ 371 (c)(1),
(2) Date: Oct. 18, 2021

(87) PCT Pub. No.: WO2020/219610
PCT Pub. Date: Oct. 29, 2020

(65) Prior Publication Data
US 2022/0193034 A1 Jun. 23, 2022

Related U.S. Application Data

(60) Provisional application No. 62/837,632, filed on Apr. 23, 2019.

(51) Int. Cl.
*A61K 31/397* (2006.01)
*A61P 33/02* (2006.01)
*C07D 487/04* (2006.01)

(52) U.S. Cl.
CPC ............ *A61K 31/397* (2013.01); *A61P 33/02* (2018.01); *C07D 487/04* (2013.01)

(58) Field of Classification Search
CPC ........................... A61K 31/397; C07D 487/04
See application file for complete search history.

(56) References Cited

U.S. PATENT DOCUMENTS

| | | |
|---|---|---|
| 10,059,711 B2 | 8/2018 | Comer et al. |
| 10,738,055 B2 | 8/2020 | Comer et al. |
| 11,174,260 B2 | 11/2021 | Comer et al. |
| 11,325,913 B2 | 5/2022 | Comer et al. |
| 2016/0289235 A1 | 10/2016 | Comer et al. |
| 2018/0194768 A1 | 7/2018 | Maianti et al. |
| 2019/0055252 A1 * | 2/2019 | Comer ............... C07D 487/04 |
| 2020/0095253 A1 | 3/2020 | Comer et al. |
| 2022/0033404 A1 | 2/2022 | Sibley et al. |
| 2022/0162211 A1 | 5/2022 | Comer et al. |

FOREIGN PATENT DOCUMENTS

| | | | | |
|---|---|---|---|---|
| WO | WO-2015070204 A1 * | 5/2015 | ............... | A61P 1/16 |
| WO | WO-2020061167 A1 * | 3/2020 | ........... | A61K 31/397 |

OTHER PUBLICATIONS

Kato et al., "Diversity-oriented synthesis yields novel multistage antimalarial inhibitors", 2016, Nature, 538, pp. 344-365 and Supplementary Information pp. 1-25 (Year: 2016).*
Soave et al., "Cryptosporidium and Cryptosporidiosis", 1986, Reviews of Infectious Diseases, 8, pp. 1012-1023 (Year: 1986).*
Habib et al., "Translation in Organelles of Apicomplexan Parasites", 2016, Trends in Parasitology, 32, pp. 939-952 (Year: 2016).*
PubChem CID: 86282873, Create Date: Dec. 8, 2014.
International Search Report and Written Opinion mailed Jul. 24, 2020 in corresponding PCT Patent Application No. PCT/US2020/029407 (20 pages).

* cited by examiner

*Primary Examiner* — Brenda L Coleman
*Assistant Examiner* — Madeline E Braun
(74) *Attorney, Agent, or Firm* — Greenberg Traurig, LLP; Melissa Hunter-Ensor; Scott Goncher

(57) ABSTRACT

Provided herein are compounds useful for the treatment of various parasitic diseases. These compounds, as well as pharmaceutically acceptable salts thereof may be formulated in pharmaceutical compositions, veterinary compositions and may be used in methods of treatment and/or prophylaxis of diseases spread by parasites, including cryptosporidiosis.

15 Claims, 9 Drawing Sheets

COMPOUNDS AND METHODS FOR THE TREATMENT OF PARASITIC DISEASES

CROSS REFERENCE TO RELATED APPLICATIONS

The present application is the National Phase of PCT/US2020/029407, filed Apr. 22, 2020, which claims priority to U.S. App. No. 62/837,632, filed Apr. 23, 2019, each of which is hereby incorporated by reference in their entirety.

STATEMENT OF FEDERALLY SPONSORED RESEARCH

This invention was made with government support under Grant Number AI109725 awarded by the National Institutes of Health. The government has certain rights in the invention.

BACKGROUND

Cryptosporidiosis is a parasitic disease and is caused by *Cryptosporidium*, a genus of protozoan parasites in the phylum Apicomplexa. Cryptosporidiosis is most commonly caused by the intracellular apicomplexan parasites *C. parvum* and *C. hominis*. It may also be caused by *C. canis, C. felts, C. meleagridis*, and *C. muris*. Cryptosporidiosis affects the distal small intestine and can affect the respiratory tract in both immunocompetent and immunocompromised individuals. Cryptosporidiosis is one of the most common waterborne diseases and is found worldwide. It can also be transmitted to other animals, including cattle, sheep, pigs, horses, goats, and geckos. Nitazoxanide is the current standard of care for cryptosporidiosis, but the drug only exhibits partial efficacy in children and is no more effective than placebo in patients with AIDS.

SUMMARY

Disclosed herein are compounds, pharmaceutical compositions, and methods of treating or preventing parasitic diseases including *Cryptosporidium* including/using a compound as described herein. In some embodiments, these pharmaceutical compositions are formulated as veterinary compositions for use with subjects other than human. The pharmaceutical composition may comprise one or more of:

Compound 1

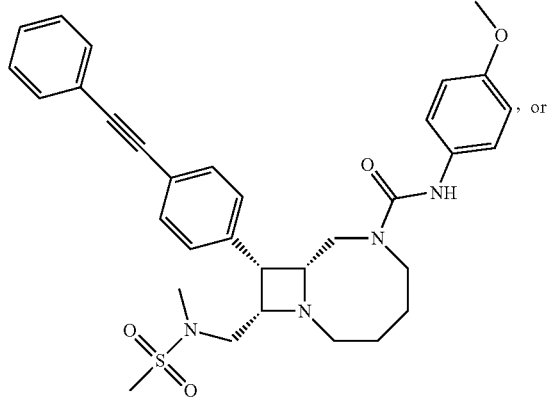

, or

Compound 2

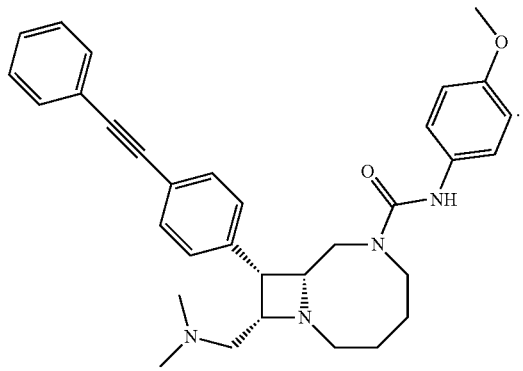

The compounds may be present in a therapeutically effective amount for the treatment of a disease caused by a parasite. For example, the compound may be present in an effective amount for the treatment or prophylaxis of a disease caused by a parasite from the genus *Cryptosporidium* (e.g., cryptosporidiosis). In some embodiments, the pharmaceutical composition may be formulated for treatment of cryptosporidiosis. Related methods of the treatment or prophylaxis of a disease in a subject are also disclosed. In some embodiments, the method of treatment or prophylaxis of a parasitic disease in a subject, comprises the step of administering to the subject an effective amount of any compound disclosed herein. In some embodiments, the effective amount of compound is formulated in a pharmaceutical composition (e.g., veterinary composition, etc.). The parasitic disease may be cryptosporidiosis. In some embodiments, the parasitotic disease is caused from the infection of a parasite selected from *C. parvum, C. hominis, C. canis, C. felts, C. meleagridis*, and *C. muris*. In some embodiments, the parasitic disease (e.g., cryptosporidiosis, etc.) is carried by *C. parvum*.

Methods for the treatment or prophylaxis of these parasitic diseases are also provided. The method may comprise administration of one or more compounds as described herein to a subject in need thereof. In some embodiments, the subject is human. In other embodiments, the subject is not human (e.g., the pharmaceutical composition is formulated as a veterinary composition). In some embodiments, the subject is a mouse, rat, rabbit, non-human primate, lizards, geckos, cow, calf, sheep, lamb, horse, foal, pig, or piglet.

These and other aspects of the invention will be apparent to those skilled in the art from the following detailed description, which is simply, by way of illustration, various modes contemplated for carrying out the invention. As will be realized, the invention is capable of additional, different obvious aspects, all without departing from the invention. Accordingly, the specification is illustrative in nature and not restrictive.

DETAILED DESCRIPTION

Definitions

Figure 1A:
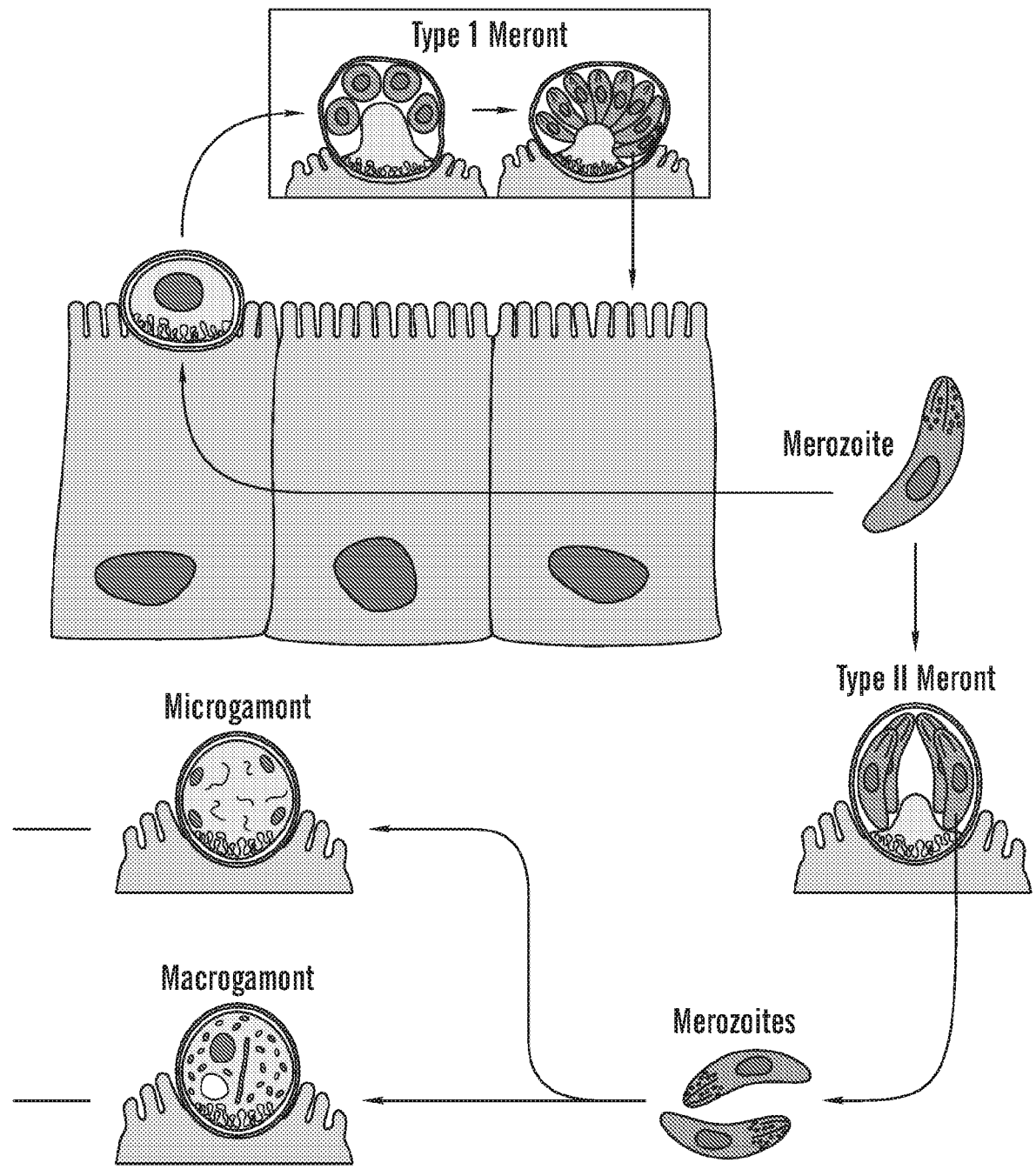
FIG. 1A is a schematic of the life cycle of *C. parvum*.

It is to be understood that the terminology employed herein is for the purpose of describing particular embodiments and is not intended to be limiting. Further, although any methods and materials similar or equivalent to those described herein can be used in the practice or testing of the disclosure.

The compounds described herein may be substituted or unsubstituted. When substituted, there will generally be, for example, 1 to 4 substituents present. These substituents may optionally form a ring with the alkyl, carbocyclic, or aryl group with which they are connected. Substituents may include, for example: carbon-containing groups such as alkyl, aryl, arylalkyl (e.g., substituted and unsubstituted phenyl, substituted and unsubstituted benzyl); halogen atoms and halogen-containing groups such as haloalkyl (e.g., trifluoromethyl); oxygen-containing groups such as alcohols (e.g., hydroxyl, hydroxyalkyl, aryl(hydroxyl)alkyl), ethers (e.g., alkoxy, cylcoalkoxy, aryloxy, alkoxyalkyl, aryloxyalkyl, methoxy, ethoxy, propoxy, isopropoxy, cyclopropoxy, etc.), aldehydes (e.g., carboxaldehyde), ketones (e.g., alkylcarbonyl, alkylcarbonylalkyl, arylcarbonyl, arylalkylcarbonyl, arylcarbonylalkyl), acids (e.g., carboxy, carboxyalkyl), acid derivatives such as esters (e.g., alkoxycarbonyl, alkoxycarbonylalkyl, alkylcarbonyloxy, alkylcarbonyloxyalkyl), amides (e.g., aminocarbonyl, mono- or di-alkylaminocarbonyl, aminocarbonylalkyl, mono- or di-alkylaminocarbonylalkyl, arylaminocarbonyl), carbamates (e.g., alkoxycarbonylamino, aryloxycarbonylamino, aminocarbonyloxy, mono- or di-alkylaminocarbonyloxy, arylminocarbonloxy) and ureas (e.g., mono- or di-alkylaminocarbonylamino or arylaminocarbonylamino); nitrogen-containing groups such as amines (e.g., amino, mono- or di-alkylamino, aminoalkyl, mono- or di-alkylaminoalkyl), azides, nitriles (e.g., cyano, cyanoalkyl), nitro; sulfur-containing groups such as thiols, thioethers, sulfoxides and sulfones (e.g., alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); heterocyclyl heteroalkyl groups, and heterocyclic groups containing one or more heteroatoms, (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

A "substituted" hydrocarbon may have as a substituent one or more hydrocarbon radicals, substituted hydrocarbon radicals, or may comprise one or more heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (F, Cl, Br, I, etc.), boron, silicon, etc. In some embodiments, heteroatoms will be selected from the group consisting of oxygen, nitrogen, sulfur, phosphorous, and halogen (F, Cl, Br, I, etc.). In some embodiments, a heteroatom or group may substitute a carbon. In some embodiments, a heteratom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo", replacing a hydrogen in the backbone or chain, etc.).

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo, $C_{1-12}$ straight chain or branched chain alkyl, $C_{2-12}$ alkenyl, $C_{2-12}$ alkynyl, $C_{3-12}$ cycloalkyl, $C_{6-12}$ aryl, $C_{3-12}$ heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Unless otherwise noted, all groups described herein optionally contain one or more common substituents, to the extent permitted by valency. Further, as used herein, the phrase "optionally substituted" means unsubstituted (e.g., substituted with an H) or substituted. As used herein, the term "substituted" means that a hydrogen atom is removed and replaced by a substituent (e.g., a common substituent). It is understood by one of ordinary skill in the chemistry art that substitution at a given atom is limited by valency. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable.

Unless otherwise indicated, unlabeled stereocenters in any structures are meant to convey a racemic mixture, or each specific stereoisomer used alone.

Compounds provided herein can have one or more asymmetric carbon atoms and can exist in the form of optically pure enantiomers, mixtures of enantiomers such as racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as chiral chromatography and separation methods based thereon. The appropriate technique and/or method for separating an enantiomer of a compound described herein from a racemic mixture can be readily determined by those of skill in the art. "Racemate" or "racemic mixture" means a mixture containing two enantiomers, wherein such mixtures exhibit no optical activity; i.e., they do not rotate the plane of polarized light. "Geometric isomer" means isomers that differ in the orientation of substituent atoms (e.g., to a carbon-carbon double bond, to a cycloalkyl ring, to a bridged bicyclic system, etc.). Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds disclosed herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9%) by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The disclosure embraces all of these forms.

The term "effective amount" or "therapeutically effective amount" of an agent, as used herein, is that amount sufficient to effect beneficial or desired results, such as clinical results, and, as such, an "effective amount" depends upon the context in which it is being applied. For example, in the context of administering an agent that is an anti-cryptosporiosis agent (e.g., nitazoxanide, etc.), an effective amount of an agent is, for example, an amount sufficient to achieve alleviation or amelioration or prevention or prophylaxis of one or more symptoms or conditions; diminishment of extent of disease, disorder, or condition; stabilized (i.e., not worsening) state of disease, disorder, or condition; preventing spread of disease, disorder, or condition (e.g., preventing the spread of *Cryptosporidium* infection, etc.); delay or slowing the progress of the disease, disorder, or condition; amelioration or palliation of the disease, disorder, or condition; and remission (whether partial or total), whether detectable or undetectable, as compared to the response obtained without administration of the agent.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein (see below).

Useful pharmaceutical carriers for the preparation of the compositions hereof, can be solids, liquids, or gases. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols may be liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

As used herein, the term "pharmaceutically acceptable salt" refers to salts of any of the compounds described herein that within the scope of sound medical judgment, are suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

As used herein, the term "subject" refers to any organism to which a composition in accordance with the disclosure may be administered, e.g., for experimental, diagnostic, prophylactic, and/or therapeutic purposes. Typical subjects include any animal (e.g., mammals such as mice, rats, rabbits, non-human primates, and humans, lizards, geckos, etc.). The subject may be domesticated animals (e.g., cows, calves, sheep, lambs, horses, foals, pigs, piglets, etc.), or animals in the family Muridae (e.g., rats, mice, etc.). A subject may seek or be in need of treatment, require treatment, be receiving treatment, may be receiving treatment in the future, or a human or animal that is under care by a trained professional for a particular disease or condition.

As used herein, and as well understood in the art, "to treat" a condition or "treatment" of the condition (e.g., the conditions described herein such as cryptosporidiosis) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gelcap, and syrup (also see below).

Other features and advantages of the disclosure are described in the following detailed description, the drawings, and the claims.

Compounds

The present disclosure provides for compounds and pharmaceutical compositions useful for the treatment of cryptosporidiosis. The disclosure also provides methods of using these compounds and compositions.

In some embodiments, the compounds may be any compound listed in Table 1, or pharmaceutically acceptable salts thereof As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

TABLE 1

| Comp. | Structure | Name |
|---|---|---|
| 1 | 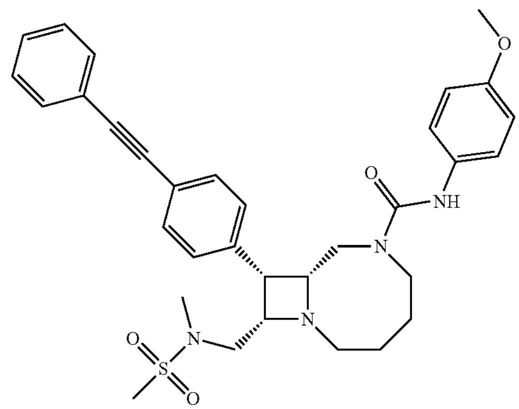 [SMILES: COc1ccc(NC(=O)N2CCCCN3[C@H](CN(C)S(C)(=O)=O)[C@H](c4ccc(C#Cc5ccccc5)cc4)[C@@H]3C2)cc1] | (8R,9R,10S)-N-(4-methoxyphenyl)-10-((N-methylmethylsulfonamido)methyl)-9-(4-(phenylethynyl)phenyl)-1,6-diazabicyclo[6.2.0]decane-6-carboxamide |
| 2 | 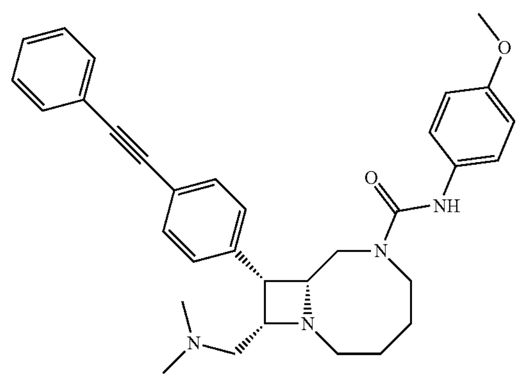 [SMILES: COc1ccc(NC(=O)N2CCCCN3[C@H](CN(C)C)[C@H](c4ccc(C#Cc5ccccc5)cc4)[C@@H]3C2)cc1] | (8R,9S,10S)-10-((dimethylamino)methyl)-N-(4-methoxyphenyl)-9-(4-(phenylethynyl)phenyl)-1,6-diazabicyclo[6.2.0]decane-6-carboxamide |

It will be understood that in the event of any inconsistency between a chemical name and formula, both compounds with the indicated chemical name and compounds with the indicated chemical structure will be considered as embraced by the invention.

The compounds of the present invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. The present invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the present invention.

The present invention also includes various hydrate and solvate forms of the compounds.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Methods

The compounds described herein are useful in the methods provided herein and, while not bound by any particular theory, are believed to exert their desirable effects through their ability to inhibit the growth of or kill a parasite from the genus *Cryptosporidium* including cryptosporidiosis. The treatment of cryptosporidiosis may include causative prophylaxis, such as preventing the spread of *Cryptosporidium* beyond infected portions of a subject (e.g. liver, intestines, respiratory tract, etc.).

Methods for the treatment or prophylaxis of a disease caused by parasites from the genus *Cryptosporidium* are provided comprising administration of one or more compounds to a subject in need thereof. In some embodiments, the composition is formulated in a pharmaceutical composition (e.g., a veterinary composition, etc.). The parasitic disease may be cryptosporidiosis. In certain embodiments, the parasite is from the genus of *Cryptosporidium*, (e.g., *C. parvum*, etc.). The subject may be human. In certain embodiments, the subject is not human (e.g., mouse, rat, rabbit, non-human primate, lizards, geckos, cow, calf, sheep, lamb, horse, foal, pig, piglet, etc.).

Pharmaceutical Compositions

1. Formulations

For use in the methods described herein, the compounds can be formulated as pharmaceutical or veterinary compositions. The formulation selected can vary depending on the subject to be treated, the mode of administration, and the type of treatment desired (e.g., prevention, prophylaxis, or therapy). A summary of formulation techniques is found in *Remington: The Science and Practice of Pharmacy, 21$^{st}$ Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference. Exemplary routes of administration and formulations are described as follows.

In the practice of the disclosed methods, the compounds (or pharmaceutically acceptable salts thereof) or compositions can be administered by any of the usual and acceptable routes and methods known in the art. The compounds or compositions can thus be administered, for example, by the enteral or gastrointestinal route (e.g., orally or rectally), topically (e.g., to the skin or an accessible mucous membrane (e.g., an intraoral (e.g., sublingual or buccal), intranasal, intrarectal, or genitourinary surface)), parenterally (e.g., by intramuscular, intravenous, subcutaneous, intraarticular, intravesicular, intrathecal, epidural, ocular, or aural application or injection), transdermally, or by inhalation (e.g., by aerosol).

The compositions can be in the form of a solid, liquid, or gas, as determined to be appropriate by those of skill in the art. Thus, as general examples, the pharmaceutical compositions may be in the form of tablets, capsules, syrups, pills, enterically coated or other protected formulations, sustained release formulations, elixirs, powders, granulates, suspensions, emulsions, solutions, gels (e.g., hydrogels), pastes, ointments, creams, plasters, transdermal patches, drenches, suppositories, enemas, injectables, implants, sprays, or aerosols.

The compositions, in general, include an effective amount of a compound described herein and one or more pharmaceutically acceptable carriers or excipients, as is well known in the art. The compositions can thus include one or more diluents, buffers, preservatives, salts, carbohydrates, amino acids, carrier proteins, fatty acids, lipids, etc. The compounds described herein may be present in amounts totaling, for example, 1-95% by weight of the total weight of the composition.

For injection, formulations can be prepared in conventional forms as liquid solutions or suspensions, or as solid forms suitable for solution or suspension in liquid prior to injection, or as emulsions. Suitable excipients for these formulations include, for example, water, saline, dextrose, and glycerol. Such compositions can also contain nontoxic auxiliary substances, such as wetting or emulsifying agents, and pH buffering agents, such as sodium acetate, sorbitan monolaurate, and so forth.

Formulations for oral use include tablets containing a compound in a mixture with one or more non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate, etc.); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol, etc.); and lubricating agents, glidants, and anti-adhesives (e.g., magnesium stearate, zinc stearate, stearic acid, silicas, hydrogenated vegetable oils, talc, etc.). Other pharmaceutically acceptable excipients can be colorants, flavoring agents, plasticizers, humectants, and buffering agents.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The pharmaceutical composition may also be formulated as a veterinary composition, intended for use with subjects other than humans. The veterinary compositions according to the present invention can be in any appropriate forms to suit the requested administration modes, for instance nasal, oral, intradermic, cutaneous or parenteral. in a certain embodiment, the composition is in a form intended for an oral administration and, for instance when the domestic animal eating, either mixed to the food ration, or directly into the mouth after meal. The veterinary compositions of the invention are in the form of a nasal, oral or injectable liquid suspension or solution, or in solid or semi-solid form, powders, pellets, capsules, granules, sugarcoated pills, gelules, sprays, cachets, pills, tablets, pastes, implants or gels. In a particular embodiment, the compositions are in the form of an oral solid form including tablets. In some embodiments, the veterinary compositions may have an effective amount of the compound for a specific species of animal (e.g., cow, lamb, goat, horse, etc.).

In various embodiments, the compositions of the invention are formulated in pellets or tablets for an oral administration. According to this type of formulation, they comprise lactose monohydrate, cellulose microcrystalline, crospovidone/povidone, aroma, compressible sugar and magnesium stearate as excipients. When the compositions are in the form of pellets or tablets, they are for instance 1 mg, 2 mg, or 4 mg torasemide pellets or tablets. Such pellets or tablets are divisible so that they can be cut to suit the posology according to the invention in one or two daily takes. In a further embodiment, the compositions of the invention are formulated in injectable solutions or suspensions for a parenteral administration. The injectable compositions are produced by mixing therapeutically efficient quantity of torasemide with a pH regulator, a buffer agent, a suspension agent, a solubilisation agent, a stabilizer, a tonicity agent and/or a preservative, and by transformation of the mixture into an intravenous, sub-cutaneous, intramuscular injection or perfusion according to a conventional method. Possibly, the injectable compositions may be lyophilized according to a conventional method. Examples of suspension agents include methylcellulose, polysorbate 80, hydroxyethylcellulose, xanthan gum, sodic carboxymethylcellulose and polyethoxylated sorbitan monolaurate. Examples of solubilisation agent include polyoxy ethylene-solidified castor oil, polysorbate 80, nicotinamide, polyethoxylated sorbitan monolaurate, macrogol and ethyl ester of caste oil fatty acid. Moreover, the stabilizer includes sodium sulfite, sodium metalsulfite and ether, while the preservative includes methyl p-hydroxybenzoate, ethyl p-hydroxybenzoate, sorbic acid, phenol, cresol and chlorocresol. An example of tonicity agent is mannitol. When preparing injectable suspensions or solutions, it is desirable to make sure that they are blood isotonic.

2. Kits

The compounds and compositions can be packaged in a kit, optionally with one or more other pharmaceutical agents. Non-limiting examples of the kits include those that contain, e.g., two or more pills, a pill and a powder, a suppository and a liquid in a vial, or two topical creams. The kits can include optional components that aid in the administration of the unit dose to subjects, such as vials for reconstituting powder forms, syringes for injection, customized IV delivery systems, or inhalers. Additionally, the unit dose kits can contain instructions for preparation and administration of the compositions. The kits can be manufactured as a single use unit dose for one subject, multiple uses for a particular subject (at a constant dose or in which the individual compounds may vary in potency as therapy progresses); or the kits can contain multiple doses suitable for administration to multiple subjects ("bulk packaging"). The kit components can be assembled in cartons, blister packs, bottles, and tubes.

3. Dosage

The dose of a compound depends on a number of factors, such as the manner of administration, the age and the body weight of the subject, and the condition of the subject to be treated, and ultimately will be decided by the attending physician or veterinarian. Such an amount of the compound, as determined by the attending physician or veterinarian, is referred to herein, and in the claims, as a "therapeutically effective amount." For example, the dose of a compound disclosed herein is typically in the range of about 1 to about 1000 mg per day. In certain implementations, the therapeutically effective amount is in an amount of from about 1 mg to about 500 mg per day.

Administration of each drug, as described herein, can, independently, be one to four times daily for one day to one year, and may even be for the life of the subject. Chronic, long-term administration may be indicated.

4. Combination Therapies

The compounds and pharmaceutical compositions can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

Examples of other drugs to combine with the compounds described herein include pharmaceuticals for the treatment of cryptosporidiosis (e.g., nitazoxanide). Other examples of drugs to combine with the compounds described herein include pharmaceuticals for the treatment of different, yet associated or related symptoms or indications. Combination methods can involve the use of the two (or more) agents formulated together or separately, as determined to be appropriate by those of skill in the art. In one example, two or more drugs are formulated together for the simultaneous or near simultaneous administration of the agents.

EXAMPLES

The following examples illustrate specific aspects of the instant description. The examples should not be construed as limiting, as the example merely provides specific understanding and practice of the embodiments and its various aspects.

Example 1: In Vivo C. parvum Assay

The NOD SCID gamma mouse model of chronic, asymptomatic C. parvum infection is used to test in vivo compound efficacy. NOD SCID gamma mice are infected with $1 \times 10^5$ C. parvum oocysts by oral gavage 5-7 days after weaning. The infected animals begin shedding oocysts in the feces 1 week after infection, which is measured by quantitative PCR (qPCR). In addition to the experimental drug regimen groups, additional negative (gavage with DMSO/methylcellulose carrier) and positive (paromomycin 2000 mg/kg once daily) control groups are included in each experiment. Mice are infected 5-7 days after weaning (day −6), infection is confirmed 1 week later (day 0), and experimental compounds are dosed by oral gavage on days 1-4. Treatment efficacy is assessed by measurement of fecal oocyst shedding by qPCR on day 5.

Example 2: C. parvum In Vitro $EC_{50}$ Assay

In vitro assays measuring the $EC_{50}$ value for C. parvum infection may be run to determine the efficacy of the compounds. For example, human ileocecal adenocarcinoma (HCT-8) cells can be obtained from ATCC and maintained in T-75 tissue culture flasks with RPMI 1640 medium with HEPES, sodium pyruvate (1 mM), and L-glutamine (ATCC) supplemented with 10% horse serum (ATCC) and 120 U/ml penicillin and 120 µg/ml streptomycin. Cells can be plated into 384-well, tissue culture-treated, black-walled, clearbottom microwell plates (BD Falcon) at a density of 8,850 cells/well and allowed to grow to confluence. The cells may then be inoculated with $5.5 \times 10^3$ primed C. parvum oocysts (Bunchgrass Farms, Deary, ID) suspended in inoculation medium (RPMI 1640 without horse serum). Oocysts may be primed for excystation by following a previously described protocol (J. Eukaryot. Microbiol. 46:56S-57S). Briefly, oocysts can be treated for 10 min with 10 mM HCl at 37° C., centrifuged, and treated with a 2 mM solution of sodium taurocholate (Sigma-Aldrich) in phosphate-buffered saline (PBS) with $Ca^{2+}$ and $Mg^{2+}$. The suspension can be incubated for 10 min at 16° C. and then diluted in inoculation medium and added to each well. Infected cells are incubated at 37° C. for 3 h, at which point an equal volume of growth medium containing 20% horse serum (total serum concentration of 10%) is produced. Compounds are diluted and assayed at fixed doses (e.g., 0.12, 0.37, 1.1, 3.3, and 10 µM, with each concentration, n=14) for the generation of $EC_{50}$ curves. In the case of final $EC_{50}$ curves, three wells are left uninfected but treated with each of the corresponding concentrations of the compound to assess for background staining. All curves are generated using the log[inhibitor] versus response variable slope equation in GraphPad Prism, with the bottom constraint set equal to 0.

Such assays were prepared on HTC-8 cells and ALI. Table 2 illustrates measured $EC_{50}$ at various time points.

TABLE 2

| Compound | $EC_{50}$ in HCT8 (µM)[a] (24 hr) | $EC_{50}$ in ALI (µM)[b] (48 hr) | Fold change[c] |
|---|---|---|---|
| Nitazoxanide | 2.190 ± 0.378 | 25.940 ± 4.137 | 11.8 |
| Compound 2 | 0.033 ± 0.009 | 0.113 ± 0.015 | 3.4 |
| Compound 1 | 0.011 ± 0.003 | 0.028 ± 0.002 | 2.5 |

Figure 1B:
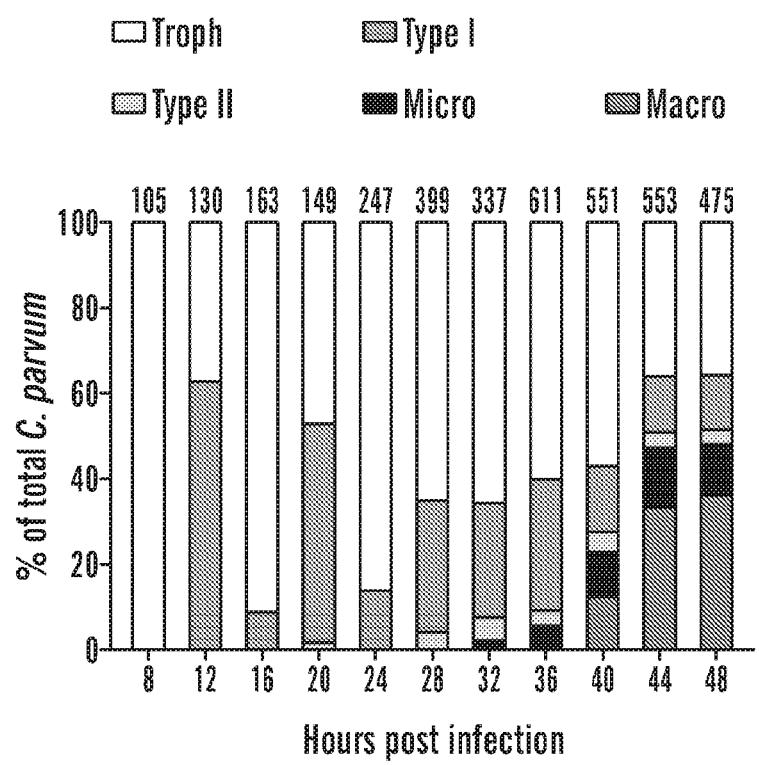
FIG. 1B shows the relative ratios of several life cycle stages of *C. parvum* at various time points following infection.
Figure 1C:
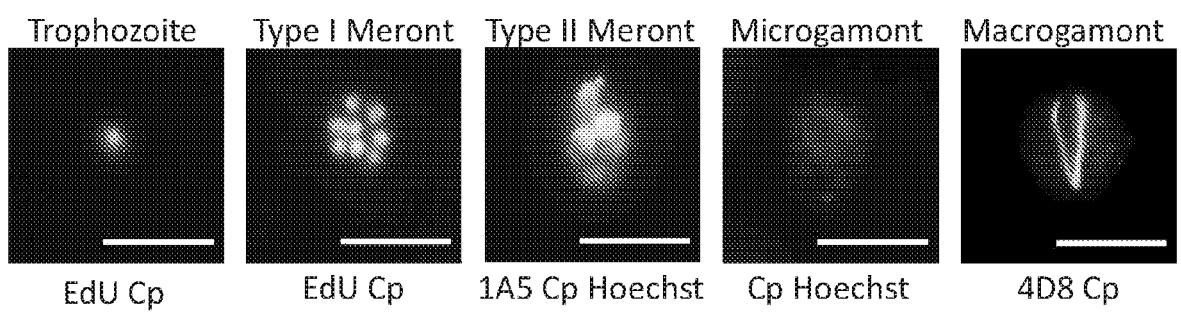
FIG. 1C is a collection of photomicrographs showing various life cycle stages of *C. parvum* present in infected cells.
Figure 2A:
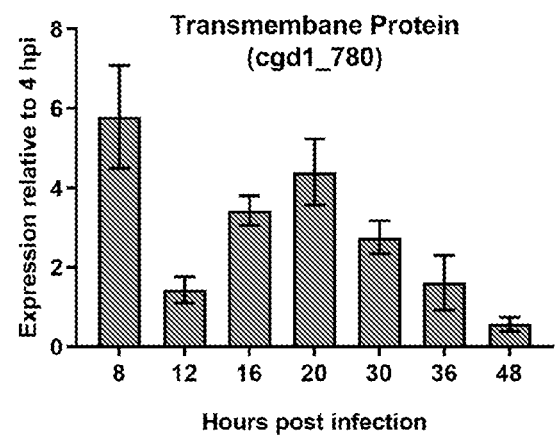
FIGS. 2A-2D illustrated the measured expression levels of proteins relevant to the *C. parvum* lifecycle at certain time points following infection.
Figure 2B:
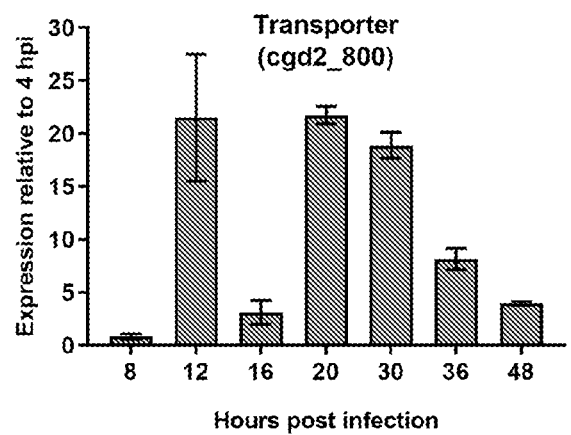
Figure 2C:
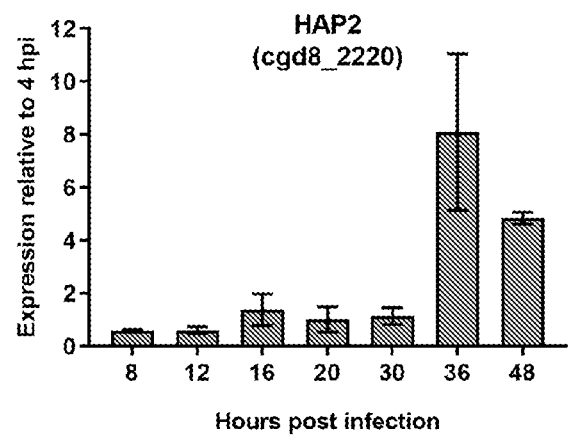
Figure 2D:
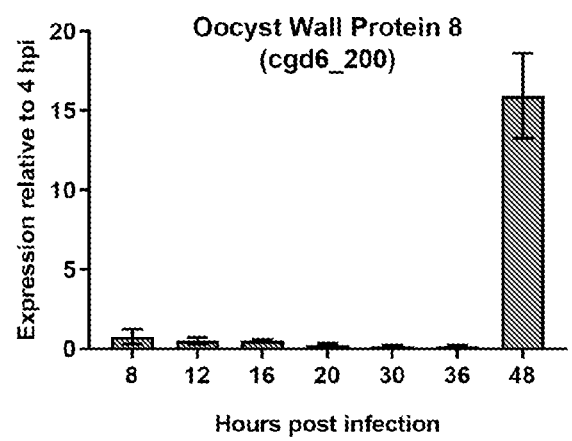

[a]Mean +/− S.D., N = 3, 9 pt curve, Log (Inhibitor) Vs Normalized Response - Variable Slope
[b]Mean +/− S.D., N = 2, 5 pt curve, Log (Inhibitor) Vs Normalized Response - Variable Slope
[c]ALI-$EC_{50}$/HCT8-$EC_{50}$ Example 3: C. parvum In Vitro Assay Treatment of infected cells occurred at various time points following infection. FIG. 1A shows a schematic of the life cycle stages of C. parvum. At various points following infection, C. parvum exists in one of these stages as indicated in FIG. 1B. The stages were identified by fluorescence tagging infected cells as shown in FIG. 1C.

The expression of various proteins associated with infection were measured from samples at time points following infection. Measured expression levels taken from infected cells of the transmembrane protein, transporter, HAP2, and oocyst wall protein 8 are shown in FIGS. 2A-2D. These results are shown relative to 4 hours post infection.

Figure 3:
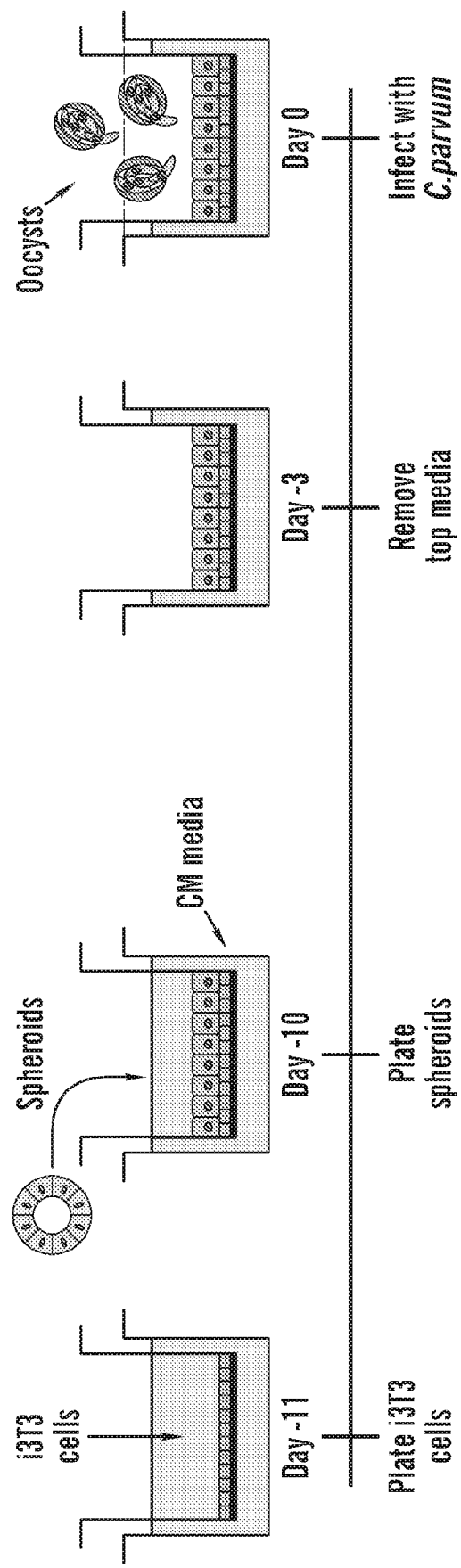
FIG. 3 is a schematic illustrating a protocol for producing an infected cell culture.
Figure 4A:
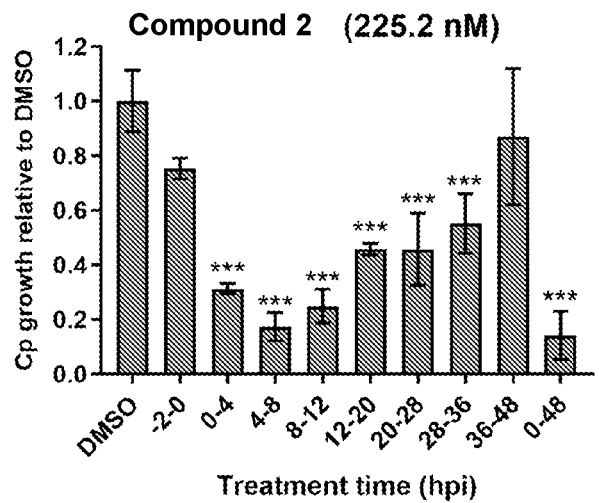
FIG. 4A illustrates the effect of varying treatment times of Compound 2 on *C. parvum* growth as compared to DMSO.
Figure 4B:
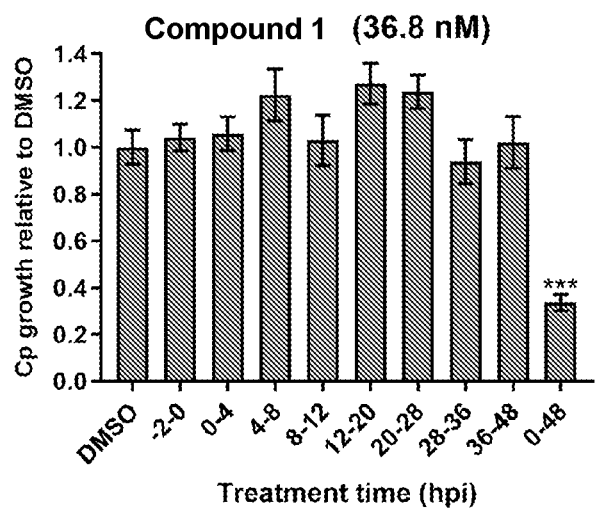
FIG. 4B illustrates the effect of varying treatment times of Compound 1 on *C. parvum* growth as compared to DMSO.
Figure 4C:
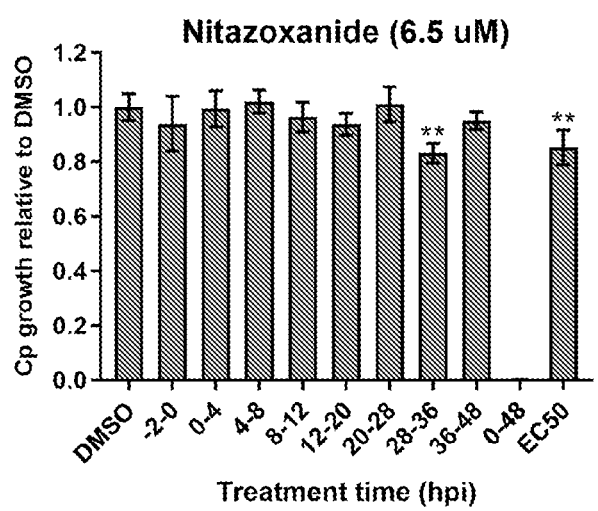
FIG. 4C illustrates the effect of varying treatment times of nitazoxanide on *C. parvum* growth as compared to DMSO.

The effect of each compound on infected samples was assessed using the culturing protocol shown in FIG. 3. Briefly, i3T3 cells were plated in CM media. Spheroids were plated on the cells. After seven days of culturing, the top CM media was removed. Three days following removal of the CM media, the cultured cells were infected with C. parvum oocysts. At various timepoints following infection, compounds as disclosed herein were applied to the infected cells. As can be seen in FIGS. 4A-C, Compound 1 at 36.8 nM, Compound 2 at 225.2 nM, and 6.5 µM of the known active nitazoxanide were applied to the cells at specific time points during infection. The growth of *C. parvum* were measure and compared to growth in DMSO without active. FIGS. 4A-C illustrate the growth following treatment during the indicated hours post infection (hpi).

Figure 5:
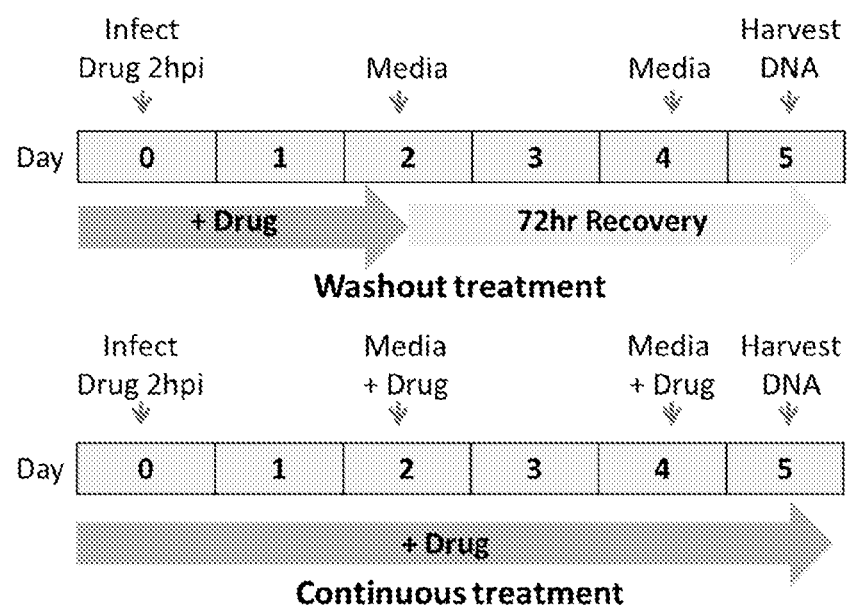
FIG. 5 is a schematic of two assay treatment regimens: washout (W/O) and continuous (C).
Figure 6:
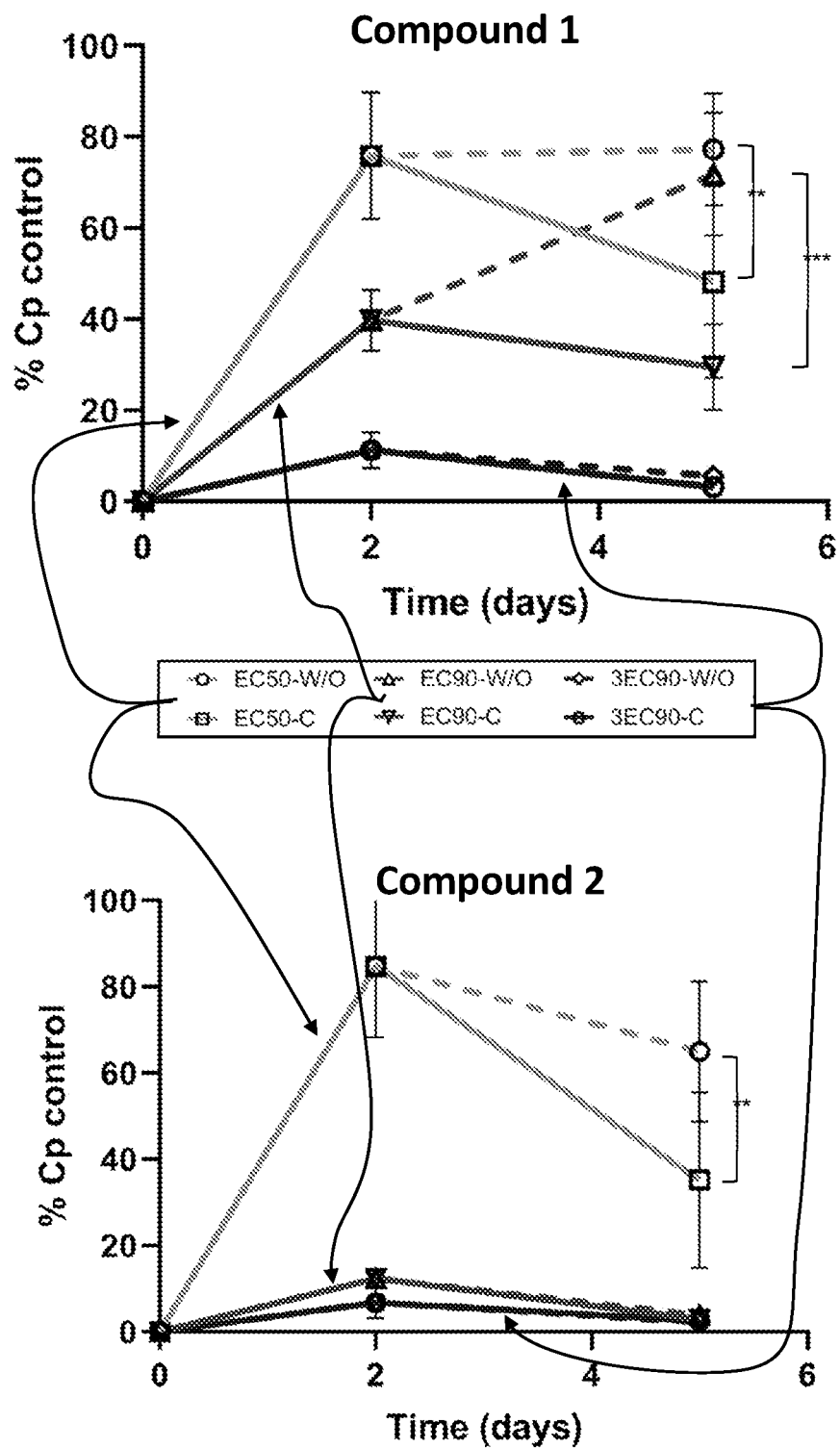
FIG. 6 illustrates the measured EC50, EC90, and 3EC90 values for Compound 1 (top) and Compound 2 (bottom). In each plot, the dashed lines represent the washout treatment and the solid lines represent the continuous treatment.

Treatment protocols were also measured in both washout and continuous treatment regimens. As shown in FIG. 5, for washout treatment (W/O), the indicated compound may be applied for a set amount of time following infection (e.g., starting two hours post infection, etc.), followed by a recovery period (e.g., 72 hours in FIG. 5). For continuous treatment, the indicated compound may be applied continuously (C) for a time period throughout one or more of *C. parvum* life stages (e.g., 5 hours post infection in FIG. 5). The $EC_{50}$, $EC_{90}$, and $3EC_{90}$ may be measured for each of these treatment modalities for the indicated compounds and compared to control. FIG. 6 (Compound 1, top) and 6 (Compound 2, bottom) illustrate these measured values for each the washout (W/O) and continuous (C) protocols. The arrows from the central legend identify the measured $EC_{50}$, $EC_{90}$, and $3EC_{90}$ data values for each compound at the specified time points. As can be seen, the W/O protocol produces more statistically significant differences from the continuous protocol at 5 days. These results are shown as a percentage of control.

Other Embodiments

The disclosures of each and every patent, patent application, and publication cited herein are hereby incorporated herein by reference in their entirety.

While the disclosure provides specific embodiments, it will be understood that it is capable of further modifications and this application is intended to cover any variations, uses, or adaptations of the following, in general, the principles described herein and including such departures from the present disclosure come within known or customary practice within the art to which the disclosure pertains and may be applied to the essential features hereinbefore set forth.

The invention claimed is:

1. A pharmaceutical composition comprising a pharmaceutically acceptable excipient and a compound having the structure of:

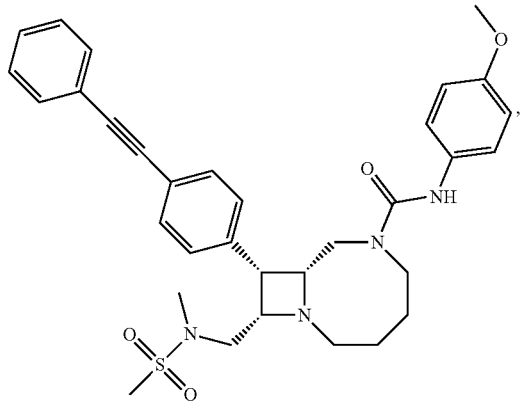

Compound 1

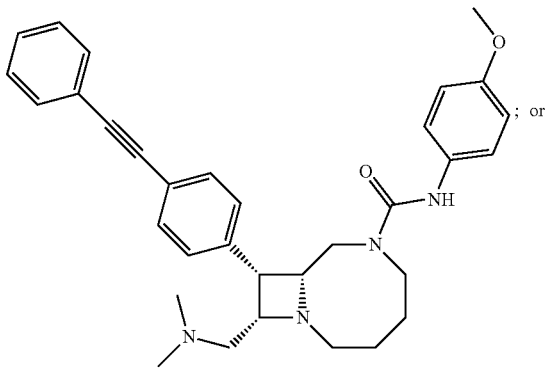

Compound 2 pharmaceutically acceptable salts thereof; wherein said compound is present in a therapeutically effective amount to treat a disease caused by a parasite from the genus *Cryptosporidium*.

2. The pharmaceutical composition according to claim 1, formulated as a veterinary composition.

3. The pharmaceutical composition according to claim 1, wherein said disease is cryptosporidiosis.

4. A method of treatment or prophylaxis of a parasitic disease caused by a parasite from the genus *Cryptosporidium* comprising the step of administering to the subject an effective amount of a compound having the structure of:

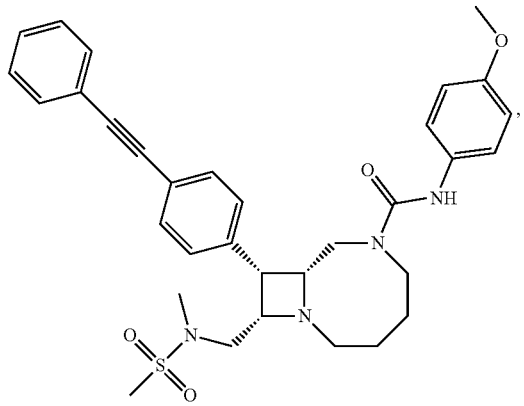

Compound 1

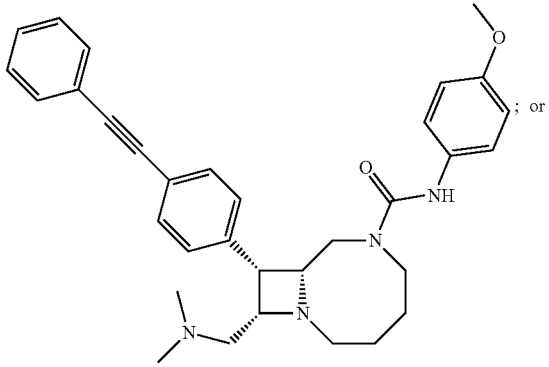

Compound 2 pharmaceutically acceptable salts thereof.

5. The method of claim 4, wherein said parasitic disease is cryptosporidiosis.

6. The method of claim 5, wherein said cryptosporidiosis is carried by *C. parvum.*

7. The method of claim 4, wherein said subject is human.

8. The method of claim 4, wherein said subject is not human.

9. The method of claim 8, wherein said subject is a mouse, rat, rabbit, non-human primate, lizard, gecko, cow, calf, sheep, lamb, horse, foal, pig, or piglet.

10. A method of treatment or prophylaxis of a parasitic disease caused from a parasite from the genus *Cryptosporidium* in a subject, comprising the step of administering to a subject the pharmaceutical composition of claim 1.

11. The method of claim 10, wherein said parasitic disease is cryptosporidiosis.

12. The method of claim 11, wherein said cryptosporidiosis is carried by *C. parvum.*

13. The method of claim 10, wherein said subject is human.

14. The method of claim 10, wherein said subject is not human.

15. The method of claim 14, wherein said subject is a mouse, rat, rabbit, non-human primate, lizard, gecko, cow, calf, sheep, lamb, horse, foal, pig, or piglet.

\* \* \* \* \*